United States Patent
Grushin et al.

(10) Patent No.: US 6,706,900 B2
(45) Date of Patent: Mar. 16, 2004

(54) PROCESS FOR PREPARING 2,5-DIFORMYLFURAN FROM CARBOHYDRATES

(75) Inventors: Vladimir Grushin, Hockessin, DE (US); Norman Herron, Newark, DE (US); Gary A. Halliday, Dover, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 87 days.

(21) Appl. No.: 10/243,337

(22) Filed: Sep. 13, 2002

(65) Prior Publication Data

US 2003/0130528 A1 Jul. 10, 2003

Related U.S. Application Data

(60) Provisional application No. 60/322,629, filed on Sep. 17, 2001.

(51) Int. Cl.⁷ .................. C07D 307/46; C07D 307/50
(52) U.S. Cl. ................................................ 549/489
(58) Field of Search .............................. 549/488, 489

(56) References Cited

U.S. PATENT DOCUMENTS

| | | |
|---|---|---|
| 4,339,387 A | 7/1982 | Fleche et al. |
| 4,590,283 A | 5/1986 | Gaset et al. |
| 4,977,283 A | 12/1990 | Leupold et al. |

FOREIGN PATENT DOCUMENTS

| | | |
|---|---|---|
| DE | 19615878 A1 | 4/1996 |
| FR | 2669636 | 11/1990 |
| JP | 55049368 | 10/1978 |
| JP | 54009260 | 1/1979 |

OTHER PUBLICATIONS

Cottier, Louis, Lewkowski, Jaroslaw, Skowronski, Romuald and Viollet, Estelle, Oxidation of 5–Hydroxymethylfurfural and Derivatives to Furanaldehydes with 2,2,6,6–Tetramethylpiperidine Oxide Radical—Co–oxidant Pairs, J. Heterocyclic Chem., 32, 927 (1995).

Moreau, C., Durand, R., Pourcheron, C. and Tichit, D., Selective oxidation of 5–hydroxymethylfurfural to 2,5–furan–discarboxaldehyde in the presence of titania supported vanadia catalysts, Stud. Surf. Sci. Catal., 108, 309–406, (1997).

Deurzen, M.P.J. van, Rantwijk, F. van and Sheldon, R.A., Chloroperozidase–Catalyzed Oxidation of 5–Hydroxymethylfurfural, J. Carbohydrate Chemistry, 16(3), 299–309 (1997).

B.F.M. Kuster, 5–Hydroxymethylfurfural (HMF). A Review Focussing on its Manufacture, starch/starcke 42 (1990) Nr. 8, S. 314–321.

Primary Examiner—Taofiq A. Solola
(74) Attorney, Agent, or Firm—Inna Y. Belopolsky

(57) ABSTRACT

2,5-Diformylfuran is prepared from a source of fructose in a one-pot, two-step reaction, in a single solvent system process, using a vanadium catalyst.

16 Claims, No Drawings

PROCESS FOR PREPARING 2,5-DIFORMYLFURAN FROM CARBOHYDRATES

This application claims benefit of Ser. No. 60/322,629 filed Sep. 17, 2001.

FIELD OF INVENTION

The present invention relates to a one-pot, two-step, catalytic process to prepare 2,5-diformylfuran from a source of fructose or other carbohydrates.

BACKGROUND 2,5-(Hydroxymethyl)furfural (HMF) is a versatile intermediate that can be obtained in high yield from biomass sources such as naturally occurring carbohydrates, including fructose, glucose, sucrose, and starch. Specifically, HMF is a conversion product of hexoses with 6 carbon atoms.

2,5-Diformylfuran (DFF) has been prepared from HMF using $CrO_3$ and $K_2Cr_2O_7$ (L. Cottier et al., *Org. Prep. Proced. Int.* (1995), 27(5), 564; JP 54009260) but these methods are expensive and result in large amounts of inorganic salts as waste. Heterogeneous catalysis using vanadium compounds has also been used, but the catalysts have shown low turnover numbers (DE 19615878, Moreau, C. et al., *Stud. Surf. Sci. Catal.* (1997), 108, 399–406). Catalytic oxidation has been demonstrated using hydrogen peroxide (M. P. J. Van Deurzen, *Carbohydrate Chem.* (1997), 16(3), 299) and dinitrogen tetraoxide (JP 55049368) which are expensive. The relatively inexpensive molecular oxygen ($O_2$) has been used with a Pt/C catalyst (U.S. Pat. No. 4,977,283) to form both DFF and furan-2,5-dicarboxylic acid (FDA), but yielded low amounts of DFF.

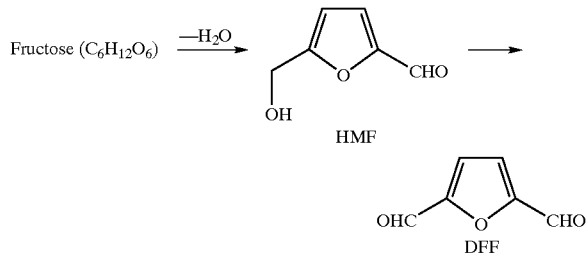

DFF is itself a useful intermediate for many compounds. DFF has been polymerized to form polypinacols and polyvinyls, and used as a starting material for the synthesis of antifungal agents, drugs, and ligands. DFF can also be used to produce unsubstituted furan. In spite of its proven usefulness, DFF is not readily available commercially.

Selective oxidation of HMF is the only industrially feasible route to DFF. A process that converts a carbohydrate to DFF that avoids the costly HMF isolation step would have an economic advantage. French patent application 2,669,636 describes a one-pot reaction using acetic anhydride in dimethyl sulfoxide for the desired process, but includes additional process steps and is sensitive to water content. After formation of HMF, water is partially removed and an additional solvent is added.

It is therefore the object of the present invention to provide a single solvent, simple, catalytic process that can be run in the presence of water to convert a carbohydrate to DFF without the isolation of HMF.

SUMMARY OF THE INVENTION

The invention is directed to a process for the preparation of 2,5-diformylfuran comprising the steps of: a) combining a source of carbohydrate with a first solvent; b) heating the reaction mixture of step (a) at a temperature sufficient to form 2,5-hydroxymethylfurfural; c) adding an oxidant and a catalytic amount of a vanadium compound to the reaction mixture of step (b); and d) heating the reaction mixture of step (c) at a temperature sufficient to form 2,5-diformylfuran; without adding an additional solvent after steps (b), (c) or (d). Preferably the source of carbohydrate is a source of fructose. More preferably the source of fructose is selected from the group consisting of crude fructose, purified fructose, a fructose-containing biomass, corn syrup, sucrose, and polyfructanes.

Also preferred is a method wherein the solvent in step (a) is dimethylsulfoxide, and in step (b), a catalyst or promoter, preferably a cation exchange resin, is added to the first reaction mixture before heating said first reaction mixture to form the second reaction mixture. The process can also further comprise the step of removing said catalyst or promoter from the second reaction mixture before step (c).

The preferred process comprises cooling the second reaction mixture to 15° C.–100° C. before step (c). Preferably the temperature of step (b) is 50° C. to 150° C. and temperature of step (d) is 120° C. to 180° C. More preferably the temperature of step (d) is 140° C. to 160° C.

A preferred vanadium compound is selected from the group consisting of vanadium oxide or vanadium phosphorus oxide; more preferred is a vanadium compound selected from the group consisting of $VO(PO_3)_2$, $(VO)_2P_2O_7$, $VOPO_4$, $VOHPO_4 \cdot 0.5H_2O$, $[(VO)_4(P_2O_7)_2(OCH_3)_4]^{-4}$ $[(C_8H_{12}N)_4]^{+4}$, $[(VO)_{12}(C_6H_5PO_3)_8(OH)_{12}]^{-4}[(C_8H_{12}N)_4]^{+4}$, $(VO)_4(C_{12}H_{10}PO_2)_2(OCH_3)_6(CH_3OH)_2$, and $V_2O_5$.

The process can further comprise the step of isolating and/or purifying the 2,5-diformylfuran formed in step (d).

DETAILED DESCRIPTION OF THE INVENTION

The present invention is a process to prepare diformylfuran (DFF), also known as furan 2,5-dicarboxaldehyde, in a single pot, two step process from a source of carbohydrate. As used herein, a "source of carbohydrate" is meant fructose, other hexoses, or any biomass that contains carbohydrates that will produce HMF upon dehydration. As used herein, by a "source of fructose" is meant fructose itself, purified or crude, or any biomass that contains fructose or precursors to fructose, such as corn syrup, sucrose, and polyfructanes. Preferred is high fructose corn syrup. As used herein, "biomass" is meant any microbial, animal or plant-based material of carbohydrate composition including herbaceous and woody energy crops, agricultural food and feed crops, agricultural crop wastes and residues, wood wastes and residues, aquatic plants, and other waste materials including some municipal wastes.

The source of carbohydrate, preferably fructose, is mixed with a suitable solvent. The fructose itself or its precursors should be at least partially soluble in the solvent used, and preferably completely dissolved. Preferred is a single solvent, but combinations of solvents may be used. By "solvent" is meant a single solvent or a combination of suitable solvents. Water may be present up to a concentration of about 5%. A suitable solvent is one in which the resulting HMF is fairly soluble, does not interfere with the dehydration reaction, and is stable at reaction conditions. Preferred solvents are dimethyl sulfoxide (DMSO), dimethylacetamide (DMA), sulfolane, N-methylpyrrolidinone (NMP), tetramethylurea (TMU), tributyl phosphate and dimethylformamide (DMF), and combinations thereof. Most preferred are dimethyl sulfoxide, tetramethylurea, or a combination thereof. The reaction mixture formed above is then heated to promote a dehydration reaction to produce HMF from fructose without adding any additional solvent. The water formed from the dehydration reaction is not considered an additional solvent.

A catalyst or promoter can optionally be added to the reaction mixture for the fructose to HMF reaction step. Catalysts include Bronsted and Lewis acids, transition metal salts and complexes, and ion exchange resins. These include, but are not limited to, oxalic acid, $H_2SO_4$, $H_3PO_4$, HCl, levulinic acid, p-toluene sulfonic acid, $I_2$, ammonium sulfate, ammonium sulfite, pyridinium phosphate, pyridinium HCl, $BF_3$ and complexes, ion-exchange resins, zeolites, and Zn, Al, Cr, Ti, Th, Zr and V salts and complexes. For other examples of catalysts and promoters, see Kuster et al., *Starch* 42 (1990), No. 8, pg. 314, which is hereby incorporated by reference. A preferred catalyst is a cation ion exchange resin, such as acid forms of Dowex® type ion-exchange resins (Dow Chemicals Co., Midlands, Mich.). More preferred are Bio-Rad AG-50W resins (Bio-Rad Laboratories, Hercules, Calif.).

The preferred temperature range will vary with solvent and catalyst or promoter used but is generally about 50° C. to about 150° C. when a catalyst or promoter is used, and is generally about 140–165° C. when a catalyst or promoter is not used. If the reaction mixture is not already at the preferred temperature it may be heated until the desired temperature is attained. The time of reaction will vary with reaction conditions and desired yield, but is generally about 1 to about 48 hours. Agitation may also be used.

In most instances, the reaction will occur faster at higher temperatures, but higher selectivities are observed at lower temperatures. At lower temperature the reaction gives better yields but may be too slow to be practical. At higher temperatures, the reaction speeds up but also becomes less selective due to side reactions and product decomposition. Therefore, in order to obtain highest possible yields of HMF, the reaction conditions should be optimized, i.e. a temperature range should be used within which the reaction is fast enough, while producing satisfactory yields of the desired product.

The insoluble catalyst or promoter of the invention, if one is used, may be removed from the reaction mixture before proceeding to the next step. The removal can be done by any known means, such as filtering, or centrifugation and decantation. The reaction mixture can also be cooled for the removal step or before proceeding to the oxidation reaction step for ease in handling. After removal, the catalyst or promoter may be washed with additional quantities of the original solvent. The washings are then combined with the filtrate in order to minimize loss of the HMF solution produced.

The process of the invention is performed as a "one-pot" reaction. By "one-pot" reaction is meant that the HMF formed in the first two step of the process is not isolated from the reaction mixture. Instead, the entire reaction mixture is used in the next step of the process. The one-pot reaction eliminates the effort and expense of the HMF isolation step. However, it will be understood to persons skilled in the art that HMF may be isolated from the reaction mixture before continuing the process herein.

A heterogeneous catalyst and an oxidant are next added to the reaction mixture formed above. It is important to note that no additional solvent is added to the reaction mixture at this time. By "additional solvent" is meant a solvent that is different than the solvent that was originally combined with the source of carbohydrate in the first step of the process. Drying of the reaction mixture may be beneficial but is not necessary.

The catalyst comprises a vanadium oxide or vanadium phosphorus oxide compound. Other anions or ligands may be present in the vanadium compound. Suitable catalysts include, but are not limited to, $VO(PO_3)_2$, $(VO)_2P_2O_7$, gamma-$VOPO_4$, delta-$VOPO_4$, $VOHPO_4 \cdot 0.5H_2O$, $[(VO)_4(P_2O_7)_2(OCH_3)_4]^{-4}[(C_8H_{12}N)_4]^{+4}$, $[(VO)_{12}(C_6H_5PO_3)_8(OH)_{12}]^{-4}[(C_8H_{12}N)_4]^{+4}$, $(VO)_4(C_{12}H_{10}PO_2)_2(OCH_3)_6(CH_3OH)_2$, and $V_2O_5$. Preferred is $V_2O_5$ and $VOHPO_4 \cdot 0.5H_2O$.

The oxidant in the processes of the present invention is preferably an oxygen-containing gas or gas mixture, such as, but not limited to air. Oxygen by itself is also a preferred oxidant. Other oxidants that are suitable include hydrogen peroxide. The reaction mixture is then heated to oxidize the HMF to produce DFF, with no additional solvent added. Drying of the reaction mixture is not necessary.

The preferred temperature range will vary with catalyst used but is about 10° C.–200° C., preferably about 140° C.–160° C. As described above, the reaction will occur faster at higher temperatures, but higher selectivities are observed at lower temperatures. Because the HMF to DFF reaction is a heterogeneous reaction catalyzed by vanadium compounds, the time needed to reach approximately 100% conversion will depend, among other factors, on (i) reaction temperature, (ii) stirring efficiency, (iii) air/oxygen flow through the liquid phase, (iv) type of catalyst used, (v) catalyst amount, (vi) the amount of water produced in the first step—large quantities of water decrease catalytic activity, (vii) catalyst dispersity, (viii) presence or absence of catalytic poisons resulting from side-products formed in the first step. The time of reaction also will vary with reaction conditions and desired yield, but is generally about 1 to about 24 hours. The reaction may be conducted under pressure of air or oxygen. Agitation may also be used.

The DFF formed above may optionally be isolated from the reaction mixture using any known means, such as but not limited to liquid-liquid extraction, vacuum distillation/sublimation of DFF, and dilution with water and extraction with a suitable organic solvent, such as dichloromethane. If dimethyl sulfoxide is used as the solvent in the reaction mixture, a preferred method is liquid-liquid extraction with a solvent such as toluene, cyclohexane, or ether.

Once isolated, the DFF may be purified by any known means, such as but not limited to vacuum sublimation, filtration in dichloromethane through silica, recrystallization, and Soxhlet extraction. When dimethyl sulfoxide is the solvent used in the reaction mixture, recrystallization using a mixture of dichloromethane and a saturated hydrocarbon such as hexane is a preferred method of purification. Soxhlet extraction is also a preferred method when using an organic solvent in the reaction mixture. The preferred organic solvent for this process is cyclohexane. In such extraction, a double thimble with the space between the outer and inner thimble being filled with silica gel is utilized. The latter method is continuous and is very convenient and efficient, producing very pure, polymer-grade DFF.

EXAMPLES

Having now generally described the invention the same will be more readily understood through reference to the following examples which are provided by way of illustration, and are not intended to be limiting of the present invention, unless specified.

The following abbreviations are used herein:

| | |
|---|---|
| $C_6H_5PO_3$ | phenylphosphonate (−2 anion) |
| $C_8H_{12}N$ | 2,4,6-collidinium (+1 cation) |
| $C_{12}H_{10}PO_2$ | diphenylphosphinate (−1 anion) |
| DFF | diformylfuran |
| DMA | dimethylacetamide |
| DMF | dimethylformamide |
| DMSO | dimethyl sulfoxide |
| GC | gas chromatography |
| HMF | 2,5-(Hydroxymethyl)furfural |
| NMP | N-methylpyrrolidinone |
| TMU | Tetramethylurea |

General Procedure

A solution of fructose (Sigma Chemical Company, St. Louis, Mo., >99% (less than 0.05% glucose) in DMSO (Aldrich Chemical Co., Milwaukee Wis., 99.9%, anhydrous) was heated (80–160° C.) at stirring, in the presence or absence of a catalyst/promoter. The reaction was monitored by quantitative GC-analysis with an external standard. Once the highest yield was achieved, the reaction mixture was cooled to room temperature, filtered (if necessary), and then used for HMF to DFF oxidation as is, i.e. without HMF isolation. For the oxidation, a vanadium catalyst was added, and the mixture vigorously stirred at 150–165° C. with air bubbling through the liquid phase. The oxidation was monitored by GC analysis. After full conversion of HMF, the DFF product was isolated and purified. The isolation was performed via liquid-liquid extraction with solvents which are immiscible with DMSO and in which DFF is soluble, e.g., cyclohexane, ether, and toluene. Alternatively, the reaction mixture was diluted with water and the DFF extracted with an organic solvent, e.g., dichloromethane. Once isolated, DFF was purified to remove impurities (e.g., dimethylsulfone) by vacuum sublimation, re-crystallization from dichloromethane-hexane, or dual-thimble Soxhlet extraction with cyclohexane through silica, as described above.

Experiment 1

Formation of $VO(PO_3)_2$ 2.35 g vanadium (IV) sulfate hydrate was dissolved into 100 mL methanol and 2.31 g 85% phosphoric acid was added cautiously with good stirring. The mixture was refluxed for 2 hours then rotovapped to yield a thick blue oil. The oil was then heated to 180° C. in an open vessel to remove residual acid and the blue solid was washed well with acetone to yield a bright blue powder. This powder was then heated in flowing nitrogen at 700° C. for 24 h with intermediate regrinding of the solid. The recovered blue-grey powder had an X-ray diffraction pattern consistent with the desired phase.

Experiment 2

Formation of $VOHPO_4.0.5H_2O$ 15 g vanadium pentoxide was slurried into 900 mL isopropanol in a round bottom flask and 38 g 85% phosphoric acid was added. The mixture was stirred vigorously and refluxed under nitrogen for 24 h during which time the slurry became pale blue in color. The blue solid was filtered and collected by washing with acetone and suction dried. The X-ray diffraction pattern of the solid was consistent with the expected phase.

Experiment 3

Formation of Gamma-$VOPO_4$ 10 g of the material prepared in Experiment 2 was spread thinly in a clean quartz boat and then heated to 680° C. over a period of 6 hours in a slow (50 mL/min) flow of oxygen. The sample was then held at 680° C. for 4 h before being cooled and collected under nitrogen. The yellow solid showed an X-ray diffraction pattern consistent with gamma-$VOPO_4$.

Experiment 4

Formation of Delta-$VOPO_4$

The process of Experiment 3 was repeated except the sample was heated to 450° C. over a period of 7.5 h and held in oxygen flow, for 168 h.

Experiment 5

Formation of $(VO)_4(P_2O_7)_2(OCH_3)_4$ as the Tetracollidinium Salt 0.47 g vanadium (IV) sulfate hydrate was dissolved in 3 mL collidine and 7 mL methanol and then boiled briefly (less than 2 min). 0.18 g pyrophosphoric acid was dissolved into 5 mL methanol and added slowly to the hot solution allowing any precipitate to redissolve before further additions of the acid. The solution was gently boiled for 3 min then allowed to cool in an open container whereupon blue crystals were formed. The blue solid was collected and identified by single crystal X-ray diffraction as the desired compound formed.

Experiment 6

Formation of $(VO)_{12}(PhPO_3)_8(OH)_{12}$ as the Tetracollidinium Salt 0.47 g vanadium (IV) sulfate hydrate was mixed with 0.32 g phenylphosphonic acid as dry solids. The mixture was then dissolved into 3 mL collidine and 7 mL acetonitrile with heating and stirring. When completely dissolved, the solution was allowed to cool and blue crystals were collected by filtration. The blue solid was collected and identified by single crystal X-ray diffraction as the desired compound.

Experiment 7

Formation of $(VO)_4(Ph_2PO_2)_2(OCH_3)_6(CH_3H)_2$ 4.70 g vanadium (IV) sulfate hydrate was dissolved into 25 mL methanol inside a nitrogen filled glove box. 10 mL collidine was added with stirring and heated until everything dissolved to a homogeneous blue solution. The solution was heated close to boiling whereupon a second solution of 2.16 g diphenylphosphonic acid dissolved in 10 mL hot methanol, was slowly added. When completely mixed the solution was briefly boiled and allowed to cool and crystallize. Deep blue crystals of the product were collected by filtration and identified by single crystal X-ray diffraction.

Experiment 8

Formation of $(VO)_2P_2O_7$ on Silica 12.3 g of the material prepared in Experiment 5 was slurried into a solution of 8.5 g 1,8-bisdimethylamino-naphthalene in 50 mL methanol. The mixture was capped and stirred until everything had completely dissolved whereupon the solution was allowed to evaporate to the point where crystalline solid began to form in the solution. This solid was collected by filtration, then 10.42 g of the solid was dissolved into 50 mL methanol under nitrogen. This deep blue solution was added to 10 g silica gel powder and the slurry was stirred for 10 min before evaporating to dryness in vacuum. The blue solid was heated to 350° C. in flowing air for 1 hour and the resultant grey powder was collected and characterized by X-ray diffraction.

Example 1

Preparation of DFF from Fructose with $VOHPO_4.0.5H_2O$ as Catalyst

Fructose (11.25 g; 62.4 mmol) was dissolved in DMSO (50 mL). To this solution was added 5 g of Bio-Rad cation exchange resin AG-50W-X8, 100–200 mesh, activated by washing with acetonitrile and drying. After the mixture was stirred at 110° C. for 5 h GC analysis indicated 85% yield of HMF. The solution was cooled and the resin was filtered off. To the dark solid-free solution (43 mL) was added $VOHPO_4.0.5H_2O$ from Experiment 2 (0.39 g; 5 mol %), and the mixture was stirred with air bubbling through it at 150° C. The reaction was monitored by GC. When full conversion of HMF was observed after 13.5 h, GC analysis indicated 52% yield of DFF based on fructose. The mixture was cooled to room temperature, diluted with dichloromethane (300 mL), filtered, washed with water (3×100 mL), passed through silica, and evaporated. The yield of crude DFF as a yellow crystalline solid was 3.2 g (41% calculated on fructose used). $^1H$ NMR ($CDCl_3$, 20° C.), δ: 7.4 (s, 2H, furan H), 9.8 (s, 2H, CHO). $^{13}C$ NMR ($CD_2Cl_2$, 20° C.), δ: 120.4 (s, CH), 154.8 (s, qC), 179.7 (s, CHO). Mass-spectrum: m/z=124.

Example 2

Preparation of DFF from Fructose with $V_2O_5$ as Catalyst

Fructose (16.875 g; 93.7 mmol) was dissolved in DMSO (75 mL). To this solution was added 3.75 g of Bio-Rad cation exchange resin AG-50W-X8, 100–200 mesh ($H^+$ form), pre-washed with water and methanol, and dried. After the mixture was stirred at 80° C. for 25.5 h GC analysis indicated 77% yield of HMF. The solution was cooled and the resin was filtered off. To the dark solid-free solution (73 mL) was added $V_2O_5$ (powder, from Alfa Aesar, Ward Hill, Mass., 99.8%, 0.66 g; 5 mol %), and the mixture was stirred with air bubbling through it at 150° C. The reaction was monitored by GC. When full conversion of HMF was observed after 17 h, GC analysis indicated 67% yield of DFF based on fructose. Isolation of the product as described in Example 1 gave 4.83 g (42%) of DFF. $^1H$ NMR ($CDCl_3$, 20° C.), δ: 7.4 (s, 2H, furan H), 9.8 (s, 2H, CHO). $^{13}C$ NMR ($CD_2Cl_2$, 20° C.), δ: 120.4 (s, CH), 154.8 (s, qC), 179.7 (s, CHO). Mass-spectrum: m/z=124.

Examples 3–9

Air-oxidation of a Commercial Sample of HMF in DMSO in the Presence of Various Vanadium Catalysts A commercial sample of HMF obtained from Aldrich was air-oxidized in the presence of various vanadium catalysts. Each oxidation was run with 50 mg of a vanadium catalyst and 103 mg of HMF dissolved in 5 mL of DMSO, for 5 h at 150° C., with air bubbling through the reaction mixture. The reaction was monitored by GC. Details of these experiments are presented in Table 1. The table indicates the catalyst used, amount of DFF and amount of HMF detected after reaction, and yield of DFF based on HMF.

TABLE 1

Vanadium-catalyzed air-oxidation of HMF (Aldrich) to DFF.

| Ex. | Catalyst | Catalyst mg | Catalyst mmol | Yield DFF, mg/mL | Yield DFF, % | Unreacted HMF, mg/mL |
|---|---|---|---|---|---|---|
| 3 | $VO(PO_3)_2$ | 50 | 0.2223 | 16.6 | 82 | 0 |
| 4 | $(VO)_2P_2O_7$ on silica (1:1) | 50 | 0.0812 | 9.16 | 45 | 7.1 |
| 5 | gamma-$VOPO_4$ | 50 | 0.3088 | 15.6 | 77 | 0 |
| 6 | delta-$VOPO_4$ | 50 | 0.3088 | 16.4 | 81 | 0 |
| 7 | $VOHPO_4.0.5H_2O$ | 50 | 0.2908 | 14 | 69 | 2.5 |
| 8 | $[(VO)_4(P_2O_7)_2(OCH_3)_4]^{-4}$ $[(C_8H_{12}N)_4]^{+4}$ | 50 | 0.0426 | 14.6 | 72 | 2.2 |
| 9 | $[(VO)_{12}(C_6H_5PO_3)_8(OH)_{12}]^{-4}$ $[(C_8H_{12}N)_4]^{+4}$ | 50 | 0.0186 | 14.4 | 71 | 0 |

Examples 10–18

Air-oxidation of HMF Generated from Fructose in DMSO in the Presence of Various Vanadium Catalysts HMF was first generated from fructose in DMSO in 74% yield as described in Example 2. The DMSO solution of HMF obtained was then divided into several equal portions, to which different vanadium compounds (5 mol %) were added to catalyze the oxidation reaction. The reactions were run at 1 atm., 150° C., and monitored by GC. Results of these studies are presented in Table 2 which shows the reaction time to full conversion and the yields of DFF based on HMF and on fructose.

TABLE 2

| Ex. | Vanadium catalyst (5 mol %) | Reaction time, h | Yield of DFF based on HMF, % | Yield of DFF based on fructose, % |
|---|---|---|---|---|
| 10 | $VO(PO_3)_2$ | 19 | 49 | 36 |
| 11 | $(VO)_2P_2O_7$ on silica (1:1) | 16.5 | 60 | 44 |
| 12 | gamma-$VOPO_4$ | 19 | 56 | 41 |
| 13 | delta-$VOPO_4$ | 13 | 60 | 44 |
| 14 | $VOHPO_4.0.5H_2O$ | 13 | 61 | 45 |
| 15 | $[(VO)_4(P_2O_7)_2(OCH_3)_4]^{-4}$ $[(C_8H_{12}N)_4]^{+4}$ | 13 | 54 | 40 |
| 16 | $[(VO)_{12}(C_6H_5PO_3)_8(OH)_{12}]^{-4}$ $[(C_8H_{12}N)_4]^{+4}$ | 16.5 | 31 | 23 |

TABLE 2-continued

| Ex. | Vanadium catalyst (5 mol %) | Reaction time, h | Yield of DFF based on HMF, % | Yield of DFF based on fructose, % |
|---|---|---|---|---|
| 17 | (VO)$_4$[(C$_6$H$_5$)$_2$PO$_2$]$_2$(OCH$_3$)$_6$(CH$_3$OH)$_2$ | 16.5 | 47 | 35 |
| 18 | V$_2$O$_5$ | 13 | 58 | 43 |

Examples 19–24

Catalyzed Oxidation of HMF (Commercial) to DFF in Various Solvents

Example 4 was repeated in various solvents. HMF (0.345 g; 2.74 mmol) was mixed in 3 mL of the solvent. The reaction was run for 5 h. Because HMF is not soluble in xylenes, the poor solubility seems to have prevented oxidation from occurring. The results are shown in Table 3 which shows the amount of HMF and DFF detected (by GC) after reaction, and the yield of DFF based on HMF.

TABLE 3

| Ex. | Catalyst | Solvent | Temp. ° C. | Amount of Catalyst (mg) | DFF mg/mL | HMF mg/mL | Yield DFF, % |
|---|---|---|---|---|---|---|---|
| 19 | V$_2$O$_5$ | Tributyl phosphate | 150 | 25 | 4.2 | 65.3 | 4 |
| 20 | V$_2$O$_5$ | Dimethylformamide | 150 | 25 | 4.2 | 76.5 | 4 |
| 21 | V$_2$O$_5$ | Xylenes | 140 | 25 | ND | 18.2 | 0 |
| 22 | VOHPO$_4$.0.5H$_2$O | Tributyl phosphate | 150 | 24 | 6.0 | 52.9 | 5 |
| 23 | VOHPO$_4$.0.5H$_2$O | Dimethylformamide | 150 | 24 | 4.7 | 76.5 | 4 |
| 24 | VOHPO$_4$.0.5H$_2$O | Xylenes | 140 | 24 | ND | 77.0 | 0 |

Example 25

Fructose (16.875 g; 93.6 mmol) was dissolved in TMU (75 mL). To this solution was added 3.75 g of Bio-Rad cation exchange resin AG-50W-X8, 100–200 mesh (H$^+$ form), pre-washed with water and methanol, and dried. After the mixture was stirred under nitrogen at 90° C. for 25.5 h GC analysis indicated 44% yield of HMF. The solution was cooled and the resin was filtered off. To the dark solid-free solution was added V$_2$O$_5$ (powder, from Alfa Aesar, Ward Hill, Mass., 99.8%, 0.375 g), and the mixture was stirred with air bubbling through it at 140° C. The reaction was monitored by GC. When full conversion of HMF was observed after 16 h, the mixture was cooled to room temperature, diluted with dichloromethane (200 mL) and filtered. The solid-free solution was washed with water (4×200 mL), dried over magnesium sulfate, filtered, and evaporated. Column chromatography of the residue (silica gel) gave 3.7 g (32%) of DFF. $^1$H NMR (CDCl$_3$, 20° C.), δ: 7.4 (s, 2H, furan H), 9.8 (s, 2H, CHO). $^{13}$C NMR (CD$_2$Cl$_2$, 20 ° C.), δ: 120.4 (s, CH), 154.8 (s, qC), 179.7 (s, CHO). Mass-spectrum: m/z=124.

What is claimed is:

1. A process for preparing 2,5-diformylfuran comprising the steps of:

a) combining a source of carbohydrate with a solvent;
   b) heating the reaction mixture of step (a) at a temperature sufficient to form 2,5-hydroxymethylfurfural;
   c) adding an oxidant and a catalytic amount of a vanadium compound to the reaction mixture of step (b); and
   d) heating the reaction mixture of step (c) at a temperature sufficient to form 2,5-diformylfuran;

without adding an additional solvent after steps (b), (c) or (d).

2. The process of claim 1, wherein the source of carbohydrate is a source of fructose.

3. The process of claim 2, wherein the source of fructose is selected from the group consisting of crude fructose, purified fructose, a fructose-containing biomass, corn syrup, sucrose, and polyfructanes.

4. The process of claim 1, wherein the solvent of step (a) is selected from the group consisting of dimethyl sulfoxide, dimethylacetamide, sulfolane, N-methylpyrrolidinone, tetramethylurea, tributyl phosphate, dimethylformamide, and combinations thereof.

5. The process of claim 1, wherein the solvent of step (a) is dimethyl sulfoxide, tetramethylurea, or a combination thereof.

6. The process of claim 1, wherein in step (b), a catalyst or promoter is added to the first reaction mixture before heating said first reaction mixture to form the second reaction mixture.

7. The process of claim 5, wherein said catalyst or promoter is a cation exchange resin.

8. The process of claim 5, further comprising the step of removing said catalyst or promoter from the second reaction mixture before step (c).

9. The process of claim 1, further comprising cooling the second reaction mixture to from 15° C. to 100° C. before step (c).

10. The process of claim 1, wherein the temperature of step (b) is 50° C. to 150° C.

11. The process of claim 1, wherein the temperature of step (d) is 120° C. to 180° C.

12. The process of claim 1, wherein the temperature of step (d) is 140° C. to 160° C.

13. The process of claim 1, wherein the vanadium compound is selected from the group consisting of vanadium oxide or vanadium phosphorus oxide.

14. The process of claim 1, wherein the vanadium compound is selected from the group consisting of VO(PO$_3$)$_2$, (VO)$_2$P$_2$O$_7$, VOPO$_4$, VOHPO$_4$.0.5H$_2$O, [(VO)$_4$(P$_2$O$_7$)$_2$(OCH$_3$)$_4$]$^{-4}$[(C$_8$H$_{12}$N)$_4$]$^{+4}$, [(VO)$_{12}$(C$_6$H$_5$PO$_3$)$_8$(OH)$_{12}$]$^{-4}$[(C$_8$H$_{12}$N)$_4$]$^{+4}$, (VO)$_4$(C$_{12}$H$_{10}$PO$_2$)$_2$(OCH$_3$)$_6$(CH$_3$OH)$_2$, and V$_2$O$_5$.

15. The process of claim 1 further comprising the step of isolating the 2,5-diformylfuran formed in step (d).

16. The process of claim 15, further comprising the step of purifying the isolated 2,5-diformylfuran.

* * * * *